US010363495B2

(12) United States Patent
Urvantsau et al.

(10) Patent No.: US 10,363,495 B2
(45) Date of Patent: Jul. 30, 2019

(54) SYSTEM AND METHOD FOR AUTO DISTILLING LIQUIDS AT STRICTLY DEFINED CONDITIONS REGARDLESS OF COMPOSITION

(71) Applicant: Instrumentation Scientifique de Laboratoire—I.S.L., Verson (FR)

(72) Inventors: Viachaslau Urvantsau, Fonenay-le-Marmion (FR); Carenne Larcher, Clinchamps Sure Orne (FR)

(73) Assignee: Instrumentation Scientifique de Laboratoire—I.S.L., Verson (FR)

( * ) Notice: Subject to any disclaimer, the term of this patent is extended or adjusted under 35 U.S.C. 154(b) by 351 days.

(21) Appl. No.: 15/226,981

(22) Filed: Aug. 3, 2016

(65) Prior Publication Data

US 2018/0036648 A1    Feb. 8, 2018

(51) Int. Cl.
*B01D 3/02* (2006.01)
*B01D 3/42* (2006.01)
(Continued)

(52) U.S. Cl.
CPC ............ *B01D 3/4233* (2013.01); *B01D 3/02* (2013.01); *B01D 3/42* (2013.01); *B01D 5/006* (2013.01);
(Continued)

(58) Field of Classification Search
CPC .......... B01D 3/02; B01D 3/42; B01D 3/4233; B01D 5/006; G01J 5/04; G01N 25/14; G01N 33/2829
See application file for complete search history.

(56) References Cited

U.S. PATENT DOCUMENTS 4,250,739 A * 2/1981 Audeh ............... G01N 33/2823
                                                    374/27
4,528,635 A * 7/1985 Juodikis ................... B01D 3/42
                                                    374/27
(Continued)

FOREIGN PATENT DOCUMENTS

DE          19803711 A1    8/1999
EP          2965795 A1     1/2016

OTHER PUBLICATIONS

International Search Report and Written Opinion issued in corresponding International Application No. PCT/IB2017/001116, dated Jan. 5, 2018, 12 pages.
(Continued)

*Primary Examiner* — Jonathan Miller
(74) *Attorney, Agent, or Firm* — Snyder, Clark, Lesch & Chung, LLP

(57) ABSTRACT

A system and method for distillation of a liquid sample at atmospheric pressure for the improved prediction of the heating necessary before the initial boiling point (IBP) of the sample is detected regardless of sample composition to ensure the IBP is observed within certain time constraints. A plurality of infrared (IR) sensors provides real-time temperature control in addition to a conventional measurement of vapor temperature. One IR-sensor monitors the liquid sample temperature in the distillation flask to obtain a corrected IBP time independent of the sample properties. Another IR-sensor monitors the temperature of the rising vapor column as the vapor rises up the neck of the distillation flask. Alternatively, an IR matrix may monitor the temperature of the rising vapor column. The system and method expand the scope of samples analyzed with improved signal, reproducibility, and test accuracy and still remain within the prescribed limits of a selected standard.

20 Claims, 8 Drawing Sheets

(51) Int. Cl.
*B01D 5/00* (2006.01)
*C10G 7/12* (2006.01)
*G01N 25/14* (2006.01)
*G01J 5/04* (2006.01)
*G01N 33/28* (2006.01)
*G01N 25/08* (2006.01)
*G01N 1/40* (2006.01)

(52) U.S. Cl.
CPC ............... *C10G 7/12* (2013.01); *G01J 5/04* (2013.01); *G01N 25/14* (2013.01); *G01N 33/2829* (2013.01); *G01N 1/4022* (2013.01); *G01N 25/08* (2013.01)

(56) References Cited

U.S. PATENT DOCUMENTS

| | | | | |
|---|---|---|---|---|
| 5,589,936 | A * | 12/1996 | Uchikawa | G01N 21/636 356/450 |
| 7,556,716 | B2 * | 7/2009 | Burian | G01N 25/08 137/2 |
| 7,820,015 | B2 * | 10/2010 | Burian | G01N 25/08 202/160 |
| 8,372,247 | B2 * | 2/2013 | Urvantsau | G01N 25/14 202/160 |
| 2003/0000651 | A1 | 1/2003 | Genser | |
| 2003/0037603 | A1 | 2/2003 | Abaev et al. | |

OTHER PUBLICATIONS

De Olveira Rodrigo R et al, Analytica Chimica Acta, Jul. 2017, pp. 41-53.
ASTM D86-04b, "Standard Test Method for Distillaton of Petroleum Products at Atmospheric Pressure," ASTM International.
Spieksma, Walter, "Prediction of ASTM Method D86 Distillation of Gasolines and Naphthas according to the Fugacity-Filmmodel from Gas Chromatographic Detailed Hydocarbon Analysis," Journal of Chromatographic Science, vol. 36, Sep. 1998.

* cited by examiner

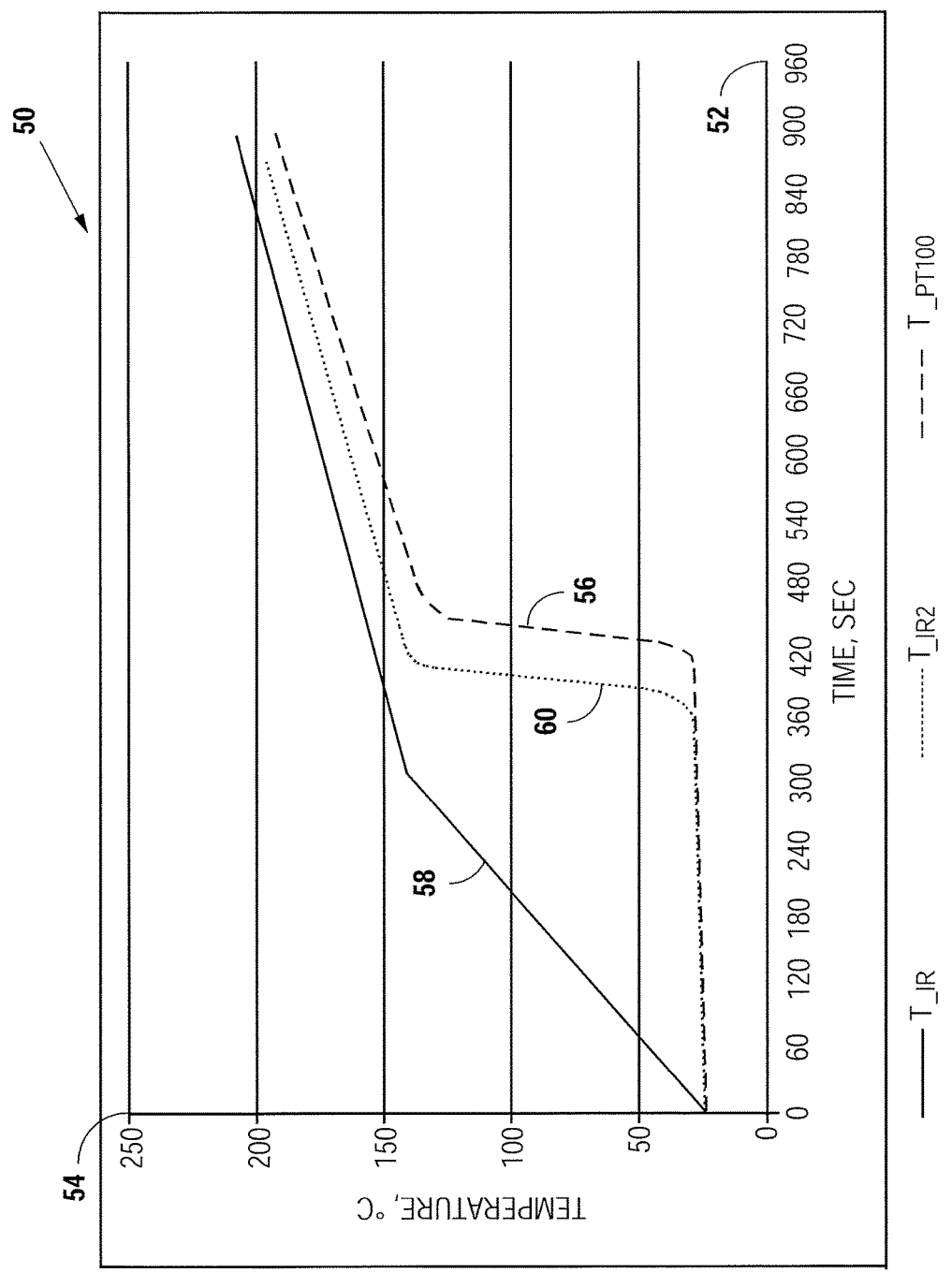

DISTILLATION OF A GASOLINE SAMPLE

SYSTEM AND METHOD FOR AUTO DISTILLING LIQUIDS AT STRICTLY DEFINED CONDITIONS REGARDLESS OF COMPOSITION

CROSS REFERENCE TO RELATED APPLICATIONS

None.

STATEMENT REGARDING FEDERALLY SPONSORED RESEARCH OR DEVELOPMENT

None.

BACKGROUND OF THE INVENTION

1. Field of the Invention

The present invention relates to distillation. More specifically, the present invention relates to the automatic distillation of liquid samples of unknown compositions at strictly defined conditions.

2. Description of the Related Art

Distillation is a common process of separating components with differing volatilities from a liquid mixture by heating and condensing a liquid sample. Generally, distillation is performed using a round bottom flask having a neck portion extending therefrom and a condenser connected to the neck portion of the flask. The other end of the condenser is connected to a receiving vessel or collecting flask. The condenser contains a cooling source, which may generally include a flowing liquid, such as running water, but may also include a solid-state cooling device, such as a Peltier device or other comparable thermoelectric cooler, around the condenser to maintain a temperature gradient there through.

Heat is provided to the distillation flask to initiate the distillation process. As the distillation progresses and the heat increases, the liquid sample begins to boil. Vapor begins to rise from the liquid sample up to the neck portion of the distillation flask. Once the vapor reaches the condenser, the vapor condenses to liquid and rolls down the length of the condenser where it is collected in the collecting flask.

During distillation, many properties of the liquid sample being distilled may be determined. Such distillation properties or characteristics can include the initial boiling point (IBP), the 5% distillation point, and the point at which there is only 5 ml of sample remaining in the distillation flask. The IBP is the temperature reading that is observed at the instant the first drop of condensate falls from the lower end of the condenser. The 5% distillation point is the temperature reading at which 5% of the initial volume of the sample has been collected in the collecting flask.

It is known in the art that distillation properties of a petroleum liquid sample may be obtained using various standard methods. For example, the American Society of Testing and Materials (ASTM) method D86 provides just such a standard method. The ASTM method D86 covers the atmospheric distillation of petroleum products using a laboratory batch distillation unit to determine quantitatively the boiling range characteristics of such products as natural gasolines, light and middle distillates and other petroleum products.

The distillation rate may be controlled through adjustments to or regulation of the heating of the liquid sample, e.g., either by increasing the heat to speed up the distillation rate or decreasing the heat to slow down the distillation rate. As such, the time of the IBP (and the 5% distillation point) may be "moved" so as to be observed within the time limits of the selected standard method of analysis, e.g., ASTM D86.

In many applications, the distillation process has been automated. For example, U.S. Pat. No. 8,372,247 (Urvantsau) (the '247 patent) discloses a method for automatic distillation of liquid petroleum samples under atmospheric pressure in a standardized distillation device. The standardized distillation device included a distillation flask, a condenser connected to the distillation flask, a collecting cylinder connected to the condenser for collecting the distillate, a thermometer for indirect measure of the temperature of a liquid sample present in the distillation flask, a thermometer for direct measurement of the temperature of evaporated vapors present in the distillation flask, a heating element and a controller to control the heating. A single-point measurement (i.e., temperature of the liquid sample) is used to predict the initial heating of unknown product. The '247 patent is incorporated by reference herein.

Prediction of the necessary heating before IBP detection is based on the temperature of the liquid sample in the distillation flask. In the prior art, this prediction is performed using a non-contacting infrared (IR) sensor to measure the temperature of the liquid in the distillation flask. The prediction of the necessary heating before the 5% distillation point is based on the temperature of the liquid sample in the distillation flask and the temperature of the vapor (measured by a standard vapor thermometer) at the point where the neck of the distillation flask connects to the condenser.

However, these predictions may not always be accurate. A dynamic of temperature distributions manifest in the neck portion of the distillation flask after the liquid sample begins to boil and vapor begins to rise in the flask. Information concerning this vapor movement during this time delay or gap (i.e., between when the liquid just begins to boil and when the moving vapor column makes direct contact with the standard vapor thermometer) is currently unmeasurable and, thus, unknown. If ascertained, however, this data (e.g., rate of column vapor movement, evaporation energy of sample) could provide additional considerations in improving the prediction of when to alter the heating temperature of the sample, e.g., either increase or decrease the heat, such that the IBP may be observed at an earlier point in time. In other words, additional measurements taken concerning the temperature distribution of the rising column of vapor (during the time delay before the vapor makes contact with the standard vapor thermometer) would improve the predictability of the necessary heating before the IBP and ensure the IBP is observed within the time limitations imposed by the selected standard because adjustments, if any—based on the additional measurements taken—to the heating of the sample can be made sooner (i.e., at some time or times prior to the vapor making contact with the standard vapor thermometer).

The rate of vapor rising at known heating must correlate with the evaporation energy of the liquid sample to be analyzed. The inventors of the present invention found that while the '247 patent continues to be a valuable method for automatic distillation of petroleum products, samples of bio-origin with significant variation of evaporation energy from petroleum distillates can be out of scope of the distillation device used. In other words, the application of the prior art is limited to "petroleum-origin fuel," i.e., products produced on the basis of petrol from a first process (e.g., distillation), secondary process, etc. . . . . . As a consequence, when non-petroleum-origin samples are analyzed using the prior art methodology, the observation of the IBP is delayed or accelerated, either case of which may be outside of the selected standard limits.

Accordingly, there is a need for the determination of the vapor temperature at an earlier time and with at least one additional sensor to measure the temperature in the area located between the liquid sample (with significant variation of evaporation energy from petroleum distillates) and the standard vapor thermometer to continuously measure the temperature distribution of the rising column of vapor. There is a further need for the determination of the rate of vapor rising at known heating before the IBP of the liquid sample is reached.

The distillation assembly of the prior art also contributes to high levels of interference (e.g., internal reflectivity and emissivity) by various components. For example, there is high level of radiation reflected from the interior wall of the collimator of the infrared (IR)-sensor monitoring the spherical part of the distillation flask. In addition, the base plate for the flask exhibits high emissivity while the IR-target area on the distillation flask exhibits low emissivity. These factors contribute to thermal interference and signal distortion, thus, affecting reproducibility and accuracy of the testing.

Accordingly, there is also a need for a distillation assembly for the automatic distillation of liquid samples having real-time control of at least two infrared temperature sensors in addition to a standardized measurement of vapor temperatures and a method for same where the start of the boiling process of the sample may be observed at an earlier point in time than what had previously been observed in the prior art. There is a further need to expand the scope of samples (beyond petroleum-based products) that can be analyzed with improved signal, reproducibility, and test accuracy and still remain within the prescribed limits of a selected standard.

BRIEF SUMMARY OF THE INVENTION

The present invention improves upon the method and apparatus disclosed in the '247 patent. The '247 patent involves the use of a single-point measurement (i.e., temperature of the liquid sample) to predict the initial heating of unknown petroleum-based product.

The present invention involves obtaining additional measurements of liquid and vapor temperatures in the distillation flask by at least two noncontact IR sensors which measure temperatures from two different areas on the surface of the distillation flask. The first area is on the spherical part of the distillation flask and corresponds to the temperature of the liquid sample. The second area is on the lower neck portion of the distillation flask above the spherical part of flask and corresponds to the vapor temperature above the sample surface. A measurement is also taken of the vapor temperature by a standard thermometer once the vapor comes in direct contact with the thermometer where the neck of the flask connects to the condenser.

The application of such additional measurements results in earlier observation of the start of the boiling process, i.e., when the liquid begins to boil, and of the vapor rising long before the drops of distillate are observed in the condenser. The estimation of the rising vapor intensity permits regulation of the heating to be made before the application of conventional regulation of distillation (i.e., adjusting the heating based on when the IBP is observed, i.e., a feedback mechanism) on the basis of, for example, the periodicity of drops in the condenser or a proportional-integral-derivative (PID) controller from the distillation rate or other similar indicia. "Regulation" means regulation of heating or prediction of necessary heating at the moment of the IBP and before the IBP. The present invention, thus, permits automatic distillation of any sample type, including samples with unknown properties.

The present invention further allows a user to perform difficult distillation analyses of unknown liquid samples without the participation of a skilled operator and without prior manual settings for heating and independent from sample properties such as heat capacity, evaporation energy, initial temperature, etc. At the same time, the present invention yields high reproducibility of automated tests and minimizes human error.

It is an object of the present invention to determine the distillation properties of a liquid sample automatically and without the necessity of manual preliminary settings or experimental iterations of settings for optimization of test parameters.

It is another object of the present invention to improve the prediction of the initial heating of an unknown sample product.

It is yet another object of the present invention to detect the start of the boiling process at an earlier time than the prior art.

It is another object of the present invention to expand the scope of analyzed samples beyond petroleum-based products.

It is another object of the present invention to remain within the analysis parameters of selected distillation standards.

The purpose of the present invention is to obtain distillation conditions within limits imposed by a selected standard, as, for example, method ASTM D86. It is the addition of a second IR sensor—which monitors the area disposed between the liquid sample and the standard vapor thermometer—to capture and continuously measure the rate of vapor rising at known heating in this area that improves upon and broadens the application of the prior art for the automatic distillation analysis beyond petroleum-based liquid samples and which may include liquid samples of non-petroleum origin (bio), IBP-high-slope products (contaminated), and high-boiling short-cut fraction products (solvents).

Several improvements to the distillation assembly minimize the amount of thermal interference observed in the prior art. Such improvements include a collimator (or thermostat) with low reflectivity, glassware with increased emissivity, a heater with decreased emissivity, and the use of double-IR measurements of temperatures at two points on the flask (e.g., on the level of the bulb and input of the neck) to detect the start of the boiling process earlier than with the current single-point measurement to improve the prediction of initial heating of unknown product regardless of composition.

BRIEF DESCRIPTION OF THE SEVERAL VIEWS OF THE DRAWINGS

FIG. 4 is a graphical representation of distillation curves illustrating the distribution of temperature curves during a standard D86 distillation using the present invention.

DETAILED DESCRIPTION OF THE INVENTION

Figure 1:
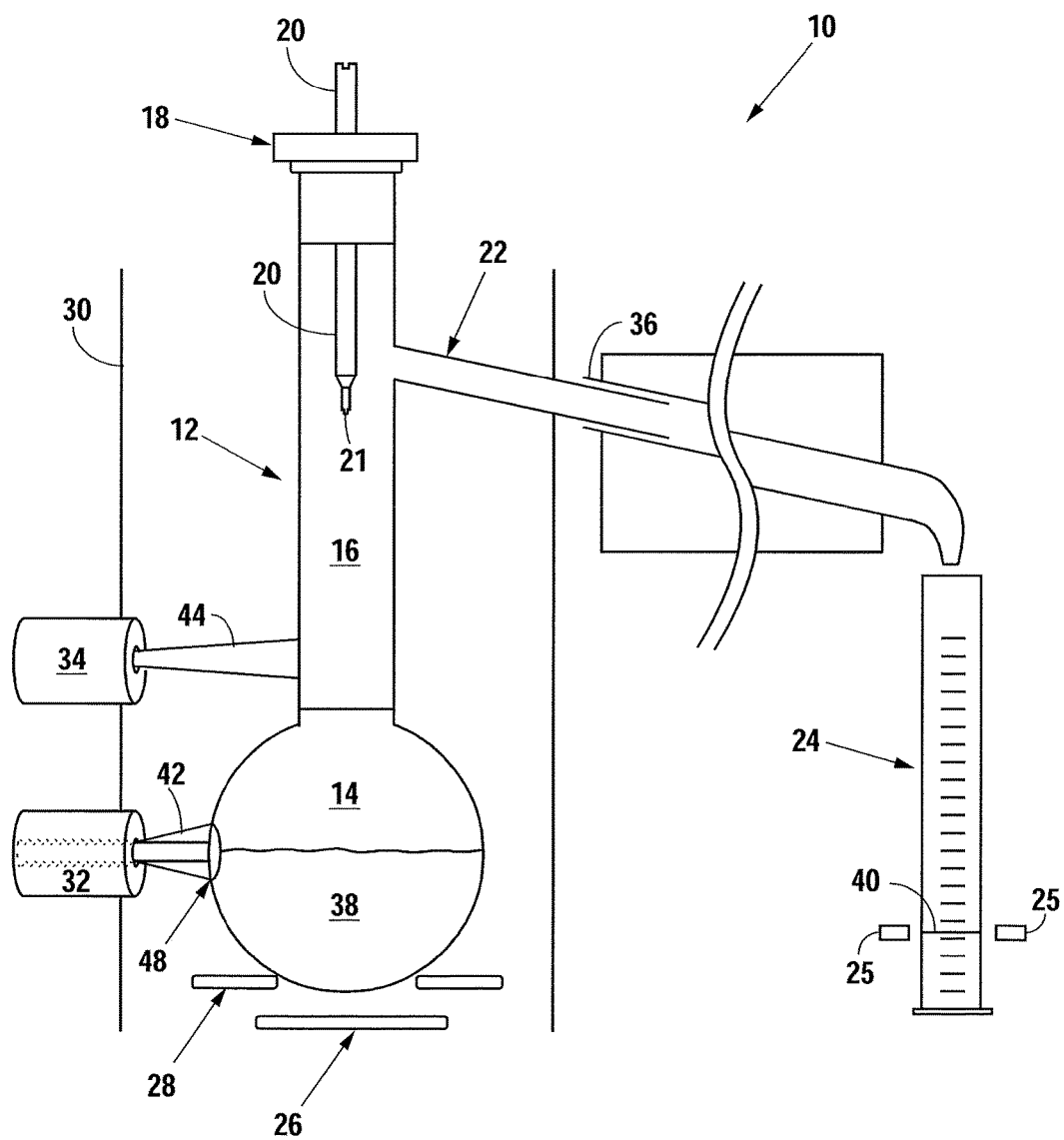
FIG. 1 is a side view of an embodiment of the present invention.

FIG. 1 depicts the distillation assembly 10 of the present invention. In one embodiment, distillation assembly 10 includes distillation flask 12 with stopper 18, thermometer 20 for measuring vapor temperature, condenser 22, cooling source 36, receiving vessel or collecting flask 24, first and second IR sensors 32 and 34, base plate 28, and heating element 26.

Distillation flask 12 has a bulb or lower rounded portion 14 and a neck portion 16. Condenser 22 connects to neck portion 16 of distillation flask 12. Stopper 18 seals distillation flask 12 at the top of neck portion 16. Thermometer 20 traverses stopper 18 via an aperture (not shown) in stopper 18 until tip 21 of thermometer 20 is just below where neck portion 16 of distillation flask 12 connects to condenser 22. Cooling source 36 surrounds condenser 22. Collecting flask 24 collects condensate or distillate 40 produced from the distillation process.

Cooling source 36 (e.g., continuous flow of water or solid-state cooling device) surrounds condenser 22 creating a temperature gradient in which accumulated vapor from distillation flask 12 condenses and rolls down condenser 22 until the condensate 40 drips into collecting flask 24. Collecting flask 24 may be in various configurations, including cylindrical, and may also be graduated to measure the quantity of distillate 40 collected. Sensor 25 determines when a predefined amount of distillate 40 has been collected, as shown in FIG. 1.

Still referring to FIG. 1, first IR sensor 32 continuously monitors and measures the temperature of liquid sample 38. IR beam 42 of first IR sensor 32 is focused on target zone 48 when taking measurements but is not in direct contact with liquid sample 38. Thermometer 20 measures the temperature of the vapor rising from the liquid sample when the vapor comes in direct contact with tip 21 of thermometer 20. Second IR sensor 34 is positioned below tip 21 of thenometer 20 and above first IR sensor 32. Preferably, second IR sensor 34 is positioned such as to have IR beam 44 continuously measuring the temperature of the vapor coming off liquid sample 38 as the vapor enters the lower part of neck portion 16 of distillation flask 12, as illustrated in FIG. 1. First and second IR sensors 32 and 34 may be mounted within the walls of housing 30 of distillation assembly 10. The present invention uses Roithner TP 339U model IR sensors. However, other comparable IR sensors may be used and still be within the contemplation of the present invention.

Perhaps the most significant improvement of the present invention is the addition of the second IR noncontact sensor. Referring now to FIG. 1, the addition of second IR sensor 34—which continuously measures the vapor temperature in the area between liquid sample 38 and thermometer 20 in the neck portion 16 of distillation flask 12—not only increases accuracy on the sample, but also expands the scope of analyzed samples. Additionally, data obtained from measurements by second IR sensor 34 facilitate the detection of the start of the boiling process earlier than was previously capable with existing systems and thus, improves the prediction of the initial heating required of an unknown product. As an added advantage, the addition of a second IR sensor also protects the bottom of the flask from overheating at the end of distillation.

In an alternative embodiment, second IR sensor 34 is replaced by an IR matrix, i.e., several sensors, or an array of IR sensors (not shown). The matrix of sensors observes the "column of signals," i.e., the line of temperatures, and the movement of the temperature gradient. Using an IR matrix, the process of vapor movement in the neck of the distillation flask is observed by measuring the temperatures of the neck, which, in turn, facilitates improvement of the regulation of temperature (e.g., preliminary heating of the liquid sample prior to IBP). Multiple measurements may be taken simultaneously of the vapor column as the vapor column rises from liquid sample 38 toward condenser 22.

The current brass thermostat or collimator around the IR sensor used in existing devices contains a smooth aperture or optical canal therein which reflects interference radiation from extra-aperture dispositions and contributes to inaccurate IR readings. The inventors found that modifying the internal surface of the optical canal became necessary to reduce the reflection of the interference (i.e., noise) radiation. Possible modifications included adjusting the fine thread or using a specific covering, e.g., graphite paint or other comparable covering.

Two collimator prototypes were developed to reduce the amount of interference reflected from the internal wall of the collimator. The first prototype contained an infrared-absorbing plastic coating on the interior wall of the optical canal of the collimator. The second contained internal threading within the optical canal of the collimator.

After testing the two collimator prototypes, the level of improvement in reducing the interference was found to be identical in both prototypes. The inventors observed a decrease of approximately 30% of IR-signal due to the elimination of interference influence. The "increment" of IR-temperature from the heated base plate became negligible.

As the two versions provided the same level of improvement, the collimator with an internally threaded optical canal was selected. This collimator also reduced the number of components (i.e., infrared-absorbing plastic coating on the interior wall of the optical canal of the collimator no longer necessary) which translated to the elimination of potential problem sites.

Figure 2:
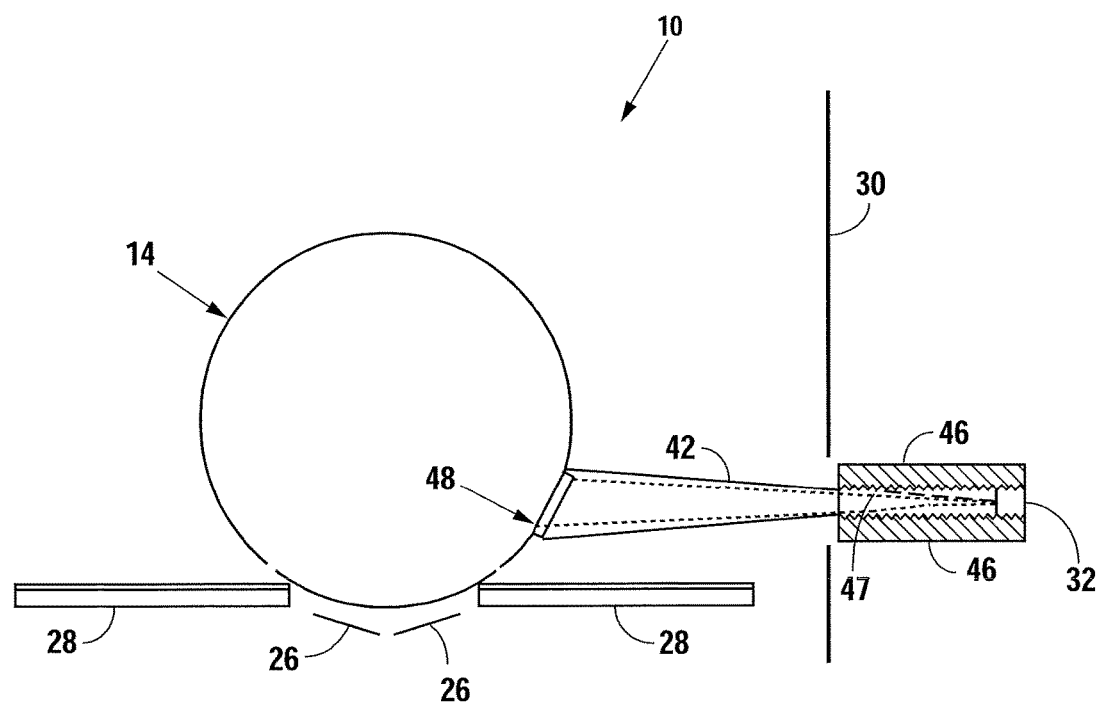
FIG. 2 shows a side perspective view of an embodiment of the present invention.

FIG. 2 shows a partial side view of distillation assembly 10 showing only first IR sensor 32. Collimator 46 of the present invention has internally threaded optical canal 47 therein. The improved collimator decreases interfering reflection from the internal wall. This modification also reduces noise interference and improves the analysis and, thus, the test results of unknown samples.

The ability of a surface to emit radiant energy (i.e., thermal radiation or heat energy) compared to that of a blackbody at the same temperature and with the same area is known as emissivity. Emissivity is the value given to materials based on the ratio of heat emitted compared to a blackbody, on a scale from zero (0) to one (1). Different materials display varying abilities to emit thermal energy. For example, a blackbody would have an emissivity value of 1 while a material that completely reflects heat would have an emissivity value of 0. Different materials would, thus, have emissivity values between 0 and 1. Therefore, the emissivity of the surface of a material is a measure of how effective the material emits energy as thermal radiation.

The emissivity of glass used in existing devices is low (e.g., 0.85) in used IR-spectrum and may be unstable in the case of contamination of the surface, small changes in the bulb shape or surface contamination. The possibility for error in testing and analysis exists due to emissivity failure which may be observed with a temperature difference of up to 17° C. This is due to high reflection of interfering IR-exposure.

To minimize error in testing from emissivity failure, and referring now to FIGS. 1 and 2, a target zone 48 for first IR sensor 32 is applied to a localized target area directly onto the glass at the bulb or lower rounded portion 14 of distillation flask 12. Target zone 48 is comprised of a paint having an increased emissivity of 0.95. During testing, the inventors found that this target zone 48 improved the stability of the IR-signal produced. In use, the error due to emissivity failure dropped substantially to <2° C. due to low reflection of interfering IR radiation. In practice, painted target zone 48 applied onto the glass at the bulb or lower rounded portion 14 of distillation flask 12 may be in any design, shape, or logo for aesthetic reasons.

Less interference is tantamount to a more stable, accurate and reproducible IR signal. The present invention, thus, increases the emissivity of the glass distillation flask (e.g., through the use of paint on a target zone) to a number closer to 1.0 which reduces the amount of interfering radiation produced thereby. This yields a more stable IR signal with improved reproducibility. Though paint may be used for target zone 48, other similar material with emissivity increasing properties may be used and still remain within the contemplation of the present invention.

The present invention also improves IR-sensor calibration to measure near-ambient temperature. The target measurement is the measurement of sample temperature in the flask just after filling and installation. This measurement can prevent error because of default in sampling temperature or can make automatic volume expansion compensation in the case of a sample temperature variation relative to a predetermined optimal value.

Prior to the present invention, the current paradigm to minimize IR interference from the base plate was to use a base plate comprised of a low thermal conductivity material, e.g., ceramic material, such as synthetic compressed calcium silicate. However, the inventors found this material fragile due to its low density.

Instead, the present invention uses a metal coating applied onto a reliable glass-ceramic base plate which, in turn, has the same desired effect, i.e., reduction in emissivity, albeit at a more pronounced level. For example, and with reference to FIG. 3A, the prior art has a target temperature at lower rounded portion 14 of distillation flask 12 at 163.6° C. while ceramic base plate 27 is heated up to a maximum temperature of 224.4° C., for a difference of 60.8° C. By way of comparison, and with reference now to FIG. 3B, the target temperature of distillation flask 12 of the present invention may be 163.7° C. at lower rounded portion 14 without degradation while metal coated glass-ceramic base plate 28 is heated up to a maximum temperature of only 202.4° C. for a difference of 38.7° C.

Figure 3A:
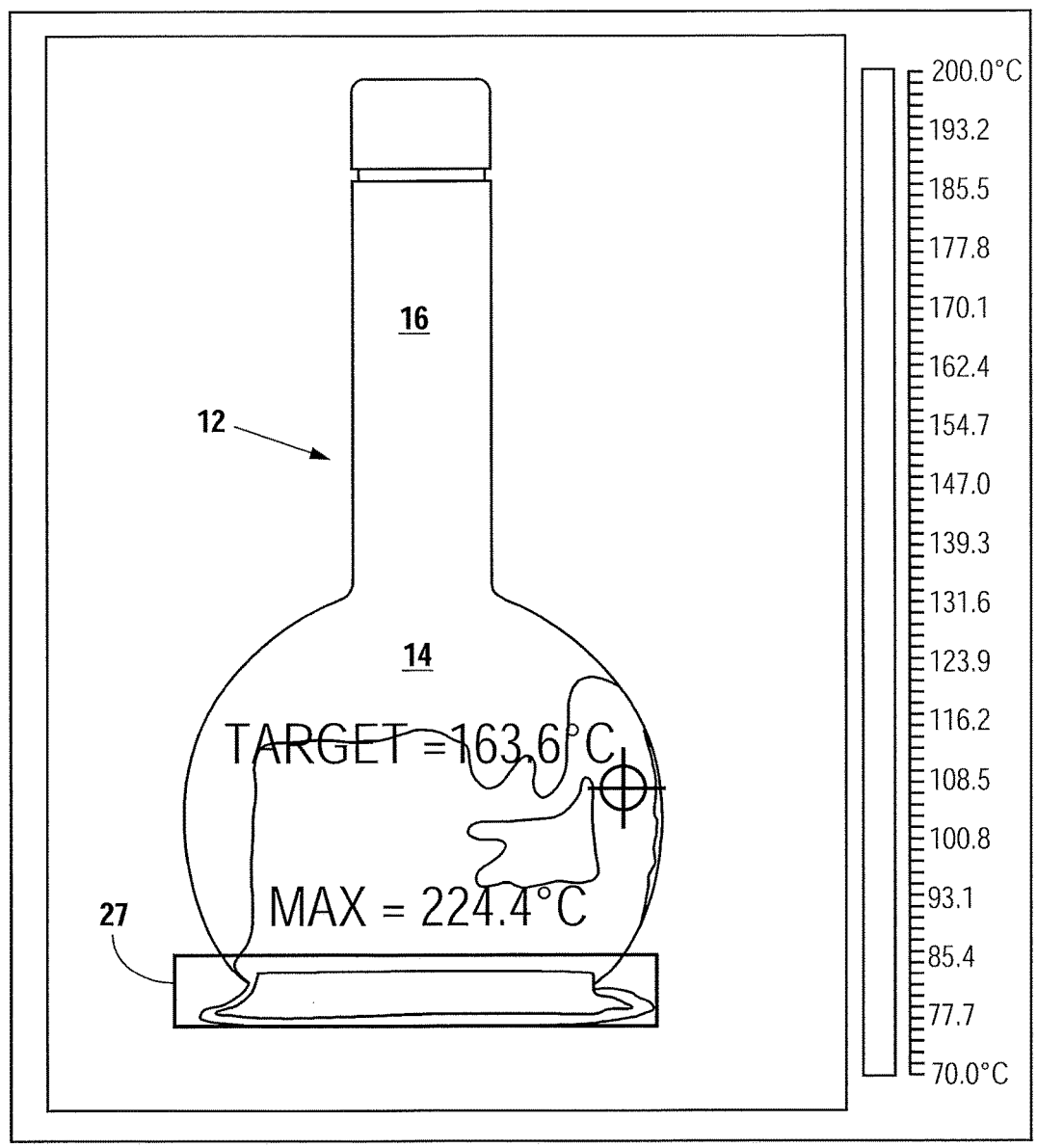
FIGS. 3A and 3B depict images used for evaluation of several solutions for decreasing emissivity of the flask support of the present invention.
Figure 3B:
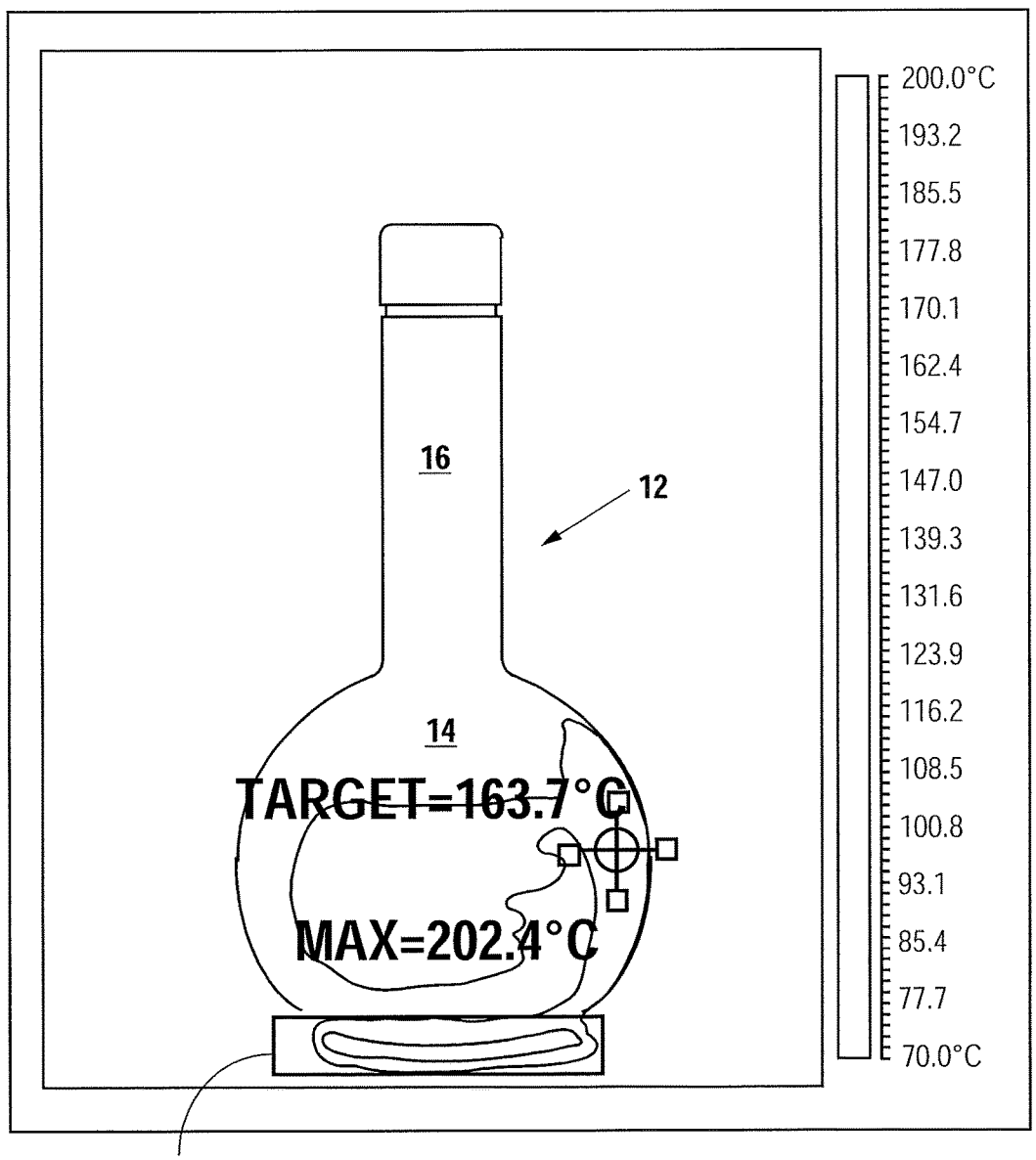

As illustrated in FIGS. 3A and 3B, improved results (i.e., reduced emissivity) were observed through the use of a metal coated glass ceramic base plate. The present invention uses a metal coated glass-ceramic material for base plate 28. However, it is noted that other comparable material with emissivity reducing properties may also be used and still remain within the contemplation of the present invention.

The present invention, thus, provides for a base plate with a reduced level of emissivity, thus, reducing or minimizing the contribution of thermal interference as compared to the prior art. The effect of this reduction in emissivity manifests itself in less noise and interference and in improved IR-signal, accuracy and reproducibility of test results.

Referring now to FIGS. 1 and 2, base plate 28 is disposed between distillation flask 12 and heater element 26. Heater element 26 of the present invention contains a heat source consisting of a halogen heater. The inventors found that this type of heater transmits up to 30% of energy by radiant energy in comparison with mainly convective heat transfer in current heaters in existing devices. The use of this halogen heater is advantageous and yields an improvement of the initial heating of the automatic distillation process. The inventors further observed an increase of reactivity of heating which, as a result, yielded an improvement of regulation of high-oxygenated gasoline products. An added advantage is that this type of heat source also minimized the likelihood and probability of damage (e.g., cracking or breaking) to the bottom of the distillation flask by decreasing the stress applied to the glass bottom of flask.

As a result of the improved distillation assembly, and as explained in further detail below, the present invention improves the preheating time and the predictability of the necessary heating before the IBP time of a liquid sample of unknown composition. The rate of vapor column movement may also be calculated, improving the 5% distillation time. Further, the drop of the vapor temperature is detected earlier permitting the optimal conditions for the final boiling point (FBP) detection to be chosen automatically.

Turning now to the method and examples of distillation with improved control of IR-temperature of the present invention, current distillation apparatuses measure the vapor temperature using a thermometer or other comparable heat detector in direct contact with the vapor. In the '247 patent, a thermometer is positioned to be in direct contact with the vapor to measure the vapor temperature in the distillation flask.

However, the inventors found that using this type of temperature sensor, while adequate, tends to delay the observation of the start of the boiling process. For example, and referring now to FIG. 4, a graphical representation (graph) 50 of the distribution of temperature curves during a standard ASTM D86 distillation using the present invention is shown. The x-axis 52 represents time (in seconds) as the distillation takes place. The y-axis 54 represents temperature (in ° C.) from beginning to end of the distillation process. Temperature curve 56 represents temperature measurements of the vapor taken by standard vapor thermometer 20 (See FIG. 1). The present invention uses a Pt100 IEC 751 platinum probe class A to measure the vapor temperature. Temperature curve 58 represents temperature measurements of the liquid sample taken by first IR sensor 32 (See FIG. 1). Temperature curve 60 represents temperature measurements of the vapor column in the neck of distillation flask 12 taken by second IR sensor 34 (See FIG. 1).

Temperature curve 56 using standard vapor thermometer 20 in direct contact with the sample vapor in the neck portion of the distillation flask shows a gradual increase in temperature for the first 420 sec. At 420 sec., a rapid increase in temperature is observed until approximately 460 sec. From 460 sec. and continuing on until 900 sec., the temperature is still observed to be increasing though the rate of increase in temperature has decreased.

Still referring to FIG. 4, temperature curve 58 taken by first IR sensor 32 shows rapid increase—almost linearly—in temperature of the liquid sample from the initial process until about 315 sec. Though the temperature still increases during the distillation process, the rate of such temperature increase decreases through to the conclusion of the distillation.

When an additional temperature sensor, such as a non-contact IR sensor (i.e., second IR sensor 34), is used to monitor and measure the vapor temperature of the vapor in the area located between the liquid sample and the standard vapor thermometer in the neck portion of the distillation flask, the same gradual increase in temperature exhibited by temperature curve 56 is still observed from the beginning of the distillation process. However, now, as shown by temperature curve 60, the rapid increase in temperature is observed at 360 sec. (a full minute earlier) and continues until about 400 sec. From 400 sec. and continuing on until 900 sec., the temperature is still observed to be increasing, though the rate of increase in temperature has decreased.

As the graph in FIG. 4 shows, the start of the boiling process, i.e., when the liquid sample begins to boil, can be detected approximately 30-90 seconds earlier than the prior art when the vapor temperature of the sample is measured in the lower neck portion of the distillation flask using a non-contacting IR sensor instead of when the vapor makes direct contact with the standard vapor thermometer higher up in the neck of the distillation flask, e.g., where the neck connects to the condenser (See FIG. 1), as in the prior art.

From this earlier detection of the vapor temperature, determination of the rate of vapor movement, and estimation of the intensity of the evaporation energy of the sample, adjustments may be made to the initial heating (e.g., increase or decrease) of the liquid sample to speed up or slow down the distillation process (i.e., distillation rate) such as to ensure the IBP will be within the specified time limits of a selected distillation standard.

Figure 5:
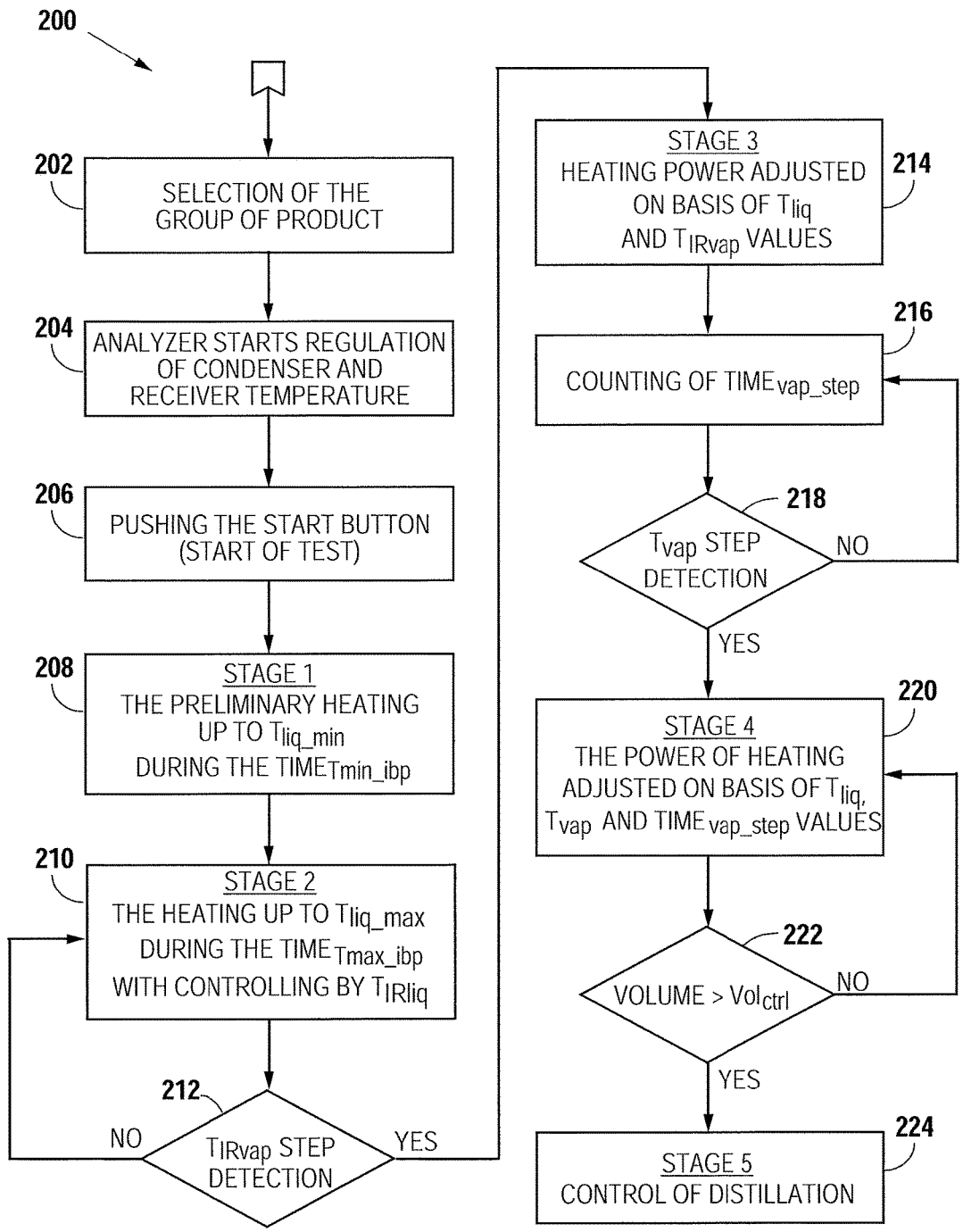
FIG. 5 depicts a flow chart of the present invention.

Referring now to FIG. 5, flow chart 200 delineates the distillation testing procedure of the present invention. The unknown liquid sample under test is prepared and placed in the distillation flask in accordance with the chosen distillation standard method (e.g., ASTM D86) and the distillation flask is installed in the distillation assembly. In one embodiment, distillation may occur automatically using an automatic analyzer. The test parameters (e.g., diameter of support plate for the distillation flask, the condenser and receiver temperatures, etc. . . . ) are set depending on the chosen distillation standard method and group of product selected. The group of products includes Groups 1-4 which group products based on their characteristics (e.g., distillate type, vapor pressure, expected IBP, etc. . . . ), as described in ASTM D86.

Beginning with block 202, the user first makes a selection of the group of product to be analyzed. In block 204, the distillation assembly, e.g., automatic analyzer, commences the regulation of the condenser and receiver temperatures. Now that the sample has been prepared and the parameters have been set, the distillation process may continue. The start of the testing or analysis begins by pushing a "Start" button or other similar initiating trigger on the distillation assembly, as depicted in block 206.

The distillation process comprises several stages. Referring still to FIG. 5, in stage 1, preliminary heating of the liquid sample commences and continues up to $T_{liq\_min}$, the minimum acceptable temperature of the liquid sample, during Time$_{Tmin\_ibp}$, as shown in block 208, where Time$_{Tmin\_ibp}$ is the minimum acceptable time from the start of heating to the IBP of the liquid sample.

Block 210 illustrates stage 2 of the distillation process where the heating of the unknown liquid sample continues up to $T_{liq\_max}$, the maximum acceptable temperature of the liquid sample, during Time$_{Tmax\_ibp}$, the maximum acceptable time from the start of heating to IBP. Whether to adjust the heating of the sample at this time is dependent upon the temperature of the liquid sample as measured by the first IR sensor. The values of $T_{liq\_min}$ were chosen to permit observation of IBP within the range of restricted times, i.e., Time$_{Tmin\_ibp}$ and Time$_{Tmax\_ibp}$.

As heating of the liquid sample continues, the second IR sensor is continuously monitoring and measuring any vapor temperature present. The second IR sensor assists in the evaluation of the dynamic of temperature distributions (previously unknown) in the area between the liquid sample and the standard vapor thermometer in the neck of the flask after boiling has begun. If no vapor temperature can be measured by the second IR sensor, the heating of the liquid sample continues, as shown in the feedback loop from block 212 to block 210. If, however, the start of boiling is observed and the resulting rising of vapor can be detected by the observation of increasing vapor temperature measured by the second IR sensor ($T_{IRvap}$), as shown in block 212, then the distillation process proceeds to stage 3.

In stage 3, the heating power to the liquid sample may be adjusted (i.e., regulated), if necessary, on the basis of the temperature of the liquid sample in the distillation flask measured by the first IR sensor on the spherical portion of the distillation flask ($T_{liq}$) and the temperature of the vapor measured by the second IR sensor at the lower part of the neck of the distillation flask ($T_{IRvap}$), as shown in block 214. In other words, as the rate of column vapor movement rising up the neck may now be evaluated by the determination of $T_{liq}$ and $T_{IRvap}$, these values allow for improvement in heat regulation. Timer Time$_{vap\_step}$ also starts counting, as shown in block 216, once the liquid sample begins boiling.

The calculation of the required heating temperature taught by the prior art ('274 patent) assumes the liquid sample is petroleum-based or otherwise of petroleum origin. As such, prior art calculations based on only a single temperature measurement (i.e., the temperature of the liquid sample in the flask measured by a single, noncontact IR sensor) are not acceptable in cases where the liquid sample is of a different origin (e.g., bio-origin fuels, etc. . . . ). However, in stage 3 of the present invention, the measurement of the vapor temperature in the lower part of the neck of the distillation flask by the second noncontact IR sensor monitoring and evaluating the rate of vapor rising improves heating regulation during increased concentration of vapor rising in the neck area of the distillation flask.

Thus, the dual temperature measurement of the present invention may evaluate the rate of vapor rising (i.e., the rate at which the "column" of vapor formed ascends the distillation flask) at known heating prior to the IBP, as the rate of vapor rising must correlate with the evaporation energy of the sample. This additional information, previously unavailable, broadens the scope (from the prior art) of the sample types that can be analyzed. Stage 3 would not be possible without the inclusion of the second IR sensor of the present invention. Nor would stage 3 be obtained using any other IR-imaging device.

Still referring to FIG. 3, as shown in block 218, as heating of the liquid sample continues, the standard vapor thermometer is continuously monitoring and measuring any direct vapor contact present. If none detected, the heating of the sample continues, as shown by the feedback loop from block 218 to block 216, and timer Time$_{vap\_step}$ continues counting, as shown in block 216. If, however, direct vapor contact occurs with the standard vapor thermometer and T$_{vap}$, the temperature of the vapor in contact with the standard vapor thermometer, is detected, timer Time$_{vap\_step}$ stops and the process proceeds to stage 4, as shown in block 220.

In Stage 4, heating of the liquid sample is adjusted on the basis of the T$_{liq}$, T$_{vap}$ and Time$_{vap\_step}$ values, as shown in block 220.

A determination of whether the volume of distillate collected is greater than the control volume (Vol$_{ctrl}$) is performed in block 222. If not, then the heating of the liquid sample is continually adjusted on the basis of the T$_{liq}$, T$_{vap}$ and Time$_{vap\_step}$ values, as shown by the feedback loop from block 222 to block 220. If the volume does exceed the control volume (Vol$_{ctrl}$), then the process proceeds to the final stage.

Block 224 shows the final stage, stage 5, where the heating control can be switched to a PID control algorithm or similar convention beginning from volume Vol$_{ctrl}$.

According to the standards (e.g., ASTM D86), there are two standard limitations of time: (1) the time from the start of test (application of heating) to the observation of the first drop of distillate in the collecting flask (i.e., the IBP), and (2) the time from the IBP to the 5% distillation point (i.e., 5% of the initial volume of sample collected as distillate). The present invention improves both.

Figure 6:
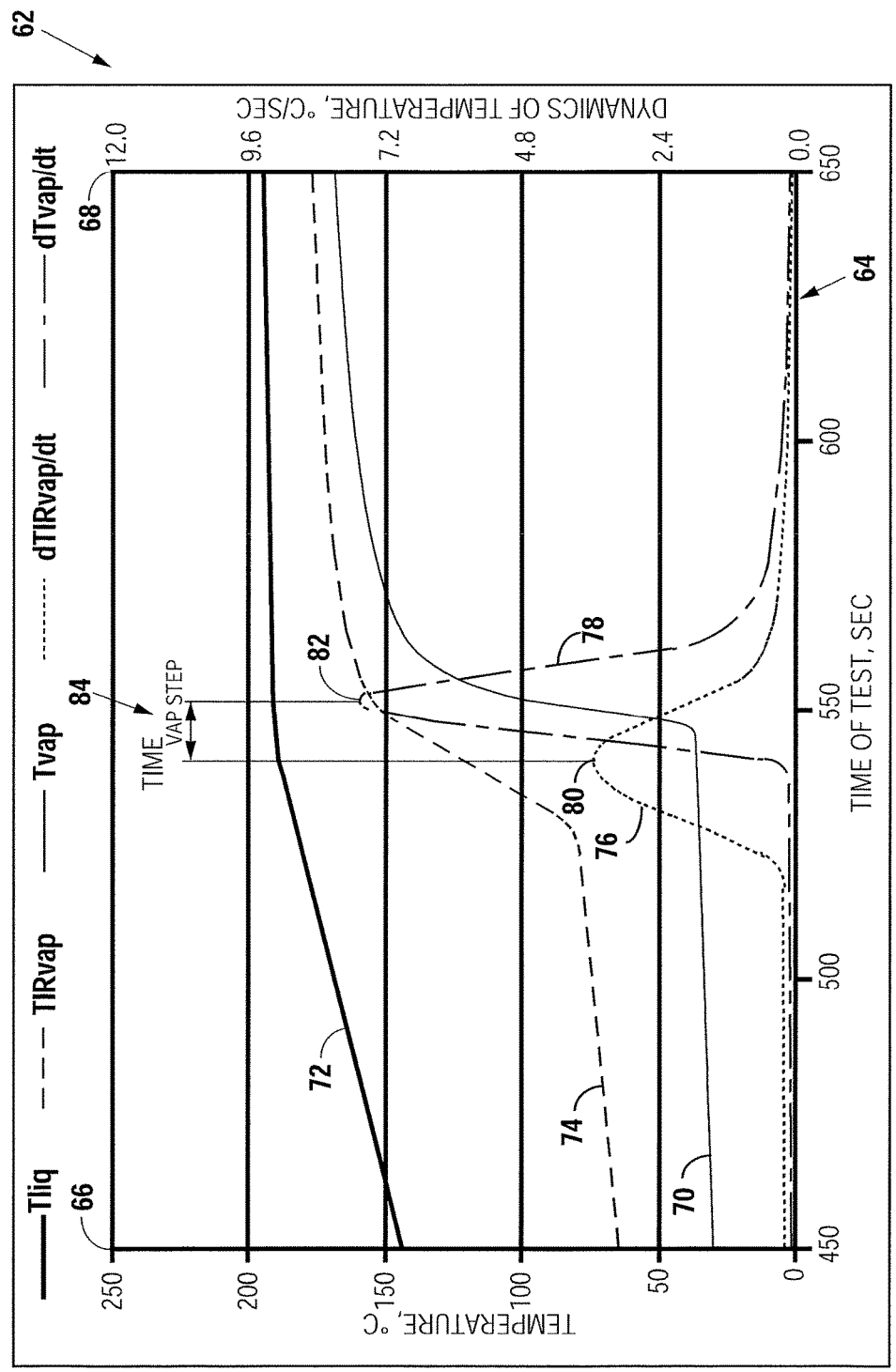
FIG. 6 depicts the distillation of a kerosene sample using an embodiment of the present invention.
Figure 7:
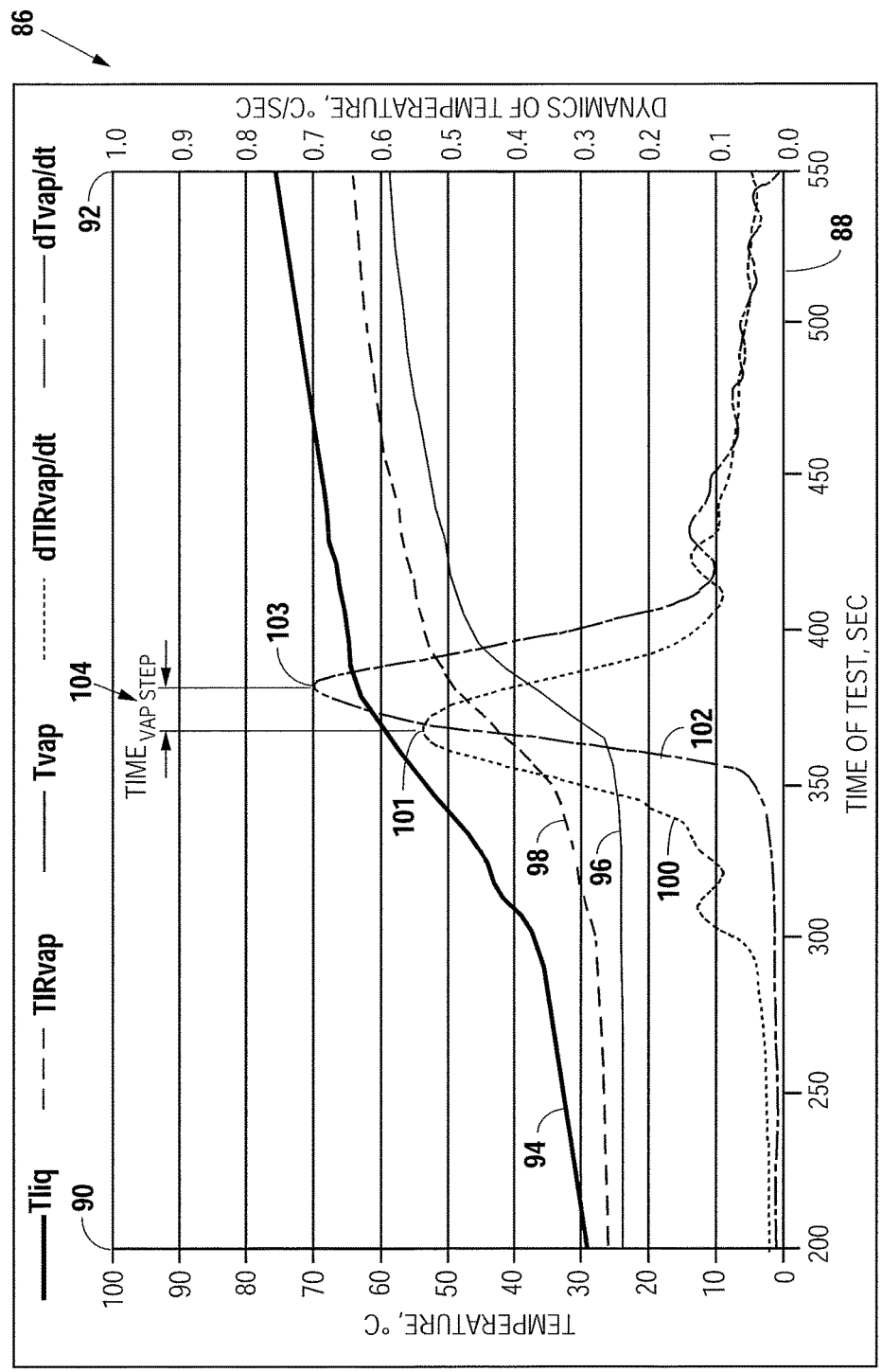
FIG. 7 depicts the distillation of a gasoline sample using an embodiment of the present invention.

FIGS. 6 and 7 illustrate distillation curves using the method of the present invention on kerosene and gasoline samples. Referring now to FIG. 6, a graphical representation 62 of a test distillation of a kerosene sample using the present invention is shown. X-axis 64 represents the time of the test (in seconds). Left y-axis 66 represents the temperature (in ° C.). Right y-axis 68 represents the dynamic of temperature (in ° C./sec). Temperature curve 72 is the value of the first IR sensor which measures the temperature of the liquid (T$_{liq}$). Temperature curve 70 is the value of temperature from the standard vapor thermometer in the upper part of the neck (T$_{vap}$). Temperature curve 74 is the value (temperature) of the vapor column in the lower portion of the neck of the distillation flask taken by the second IR sensor (T$_{IRvap}$). Curve 78 is the rate of change of the vapor temperature measured by the vapor thermometer (dT$_{vap}$/dt). Curve 76 represents the derivative of the temperature measurements of the vapor column in the neck of the distillation flask measured by the second IR sensor (i.e., the rate of change of the vapor temperature, i.e., dT$_{IRvap}$/dt).

Referring now to FIG. 7, a graphical representation (graph) 86 of the test distillation of a gasoline sample using the present invention is shown. X-axis 88 represents the time of the test (in seconds). Left y-axis 90 represents the temperature (in ° C.). Right y-axis 92 represents the dynamic of temperature (in ° C./sec). Temperature curve 94 is the value of the first IR sensor which measures the temperature of the liquid (T$_{liq}$). Temperature curve 96 is the value of temperature from standard vapor thermometer in the upper part of the neck (T$_{vap}$). Temperature curve 98 is the value (temperature) of the vapor column in the lower portion of the neck of the distillation flask taken by the second IR sensor (T$_{IRvap}$). Curve 102 is the rate of change of the vapor temperature measured by the vapor thermometer (dT$_{vap}$/dt). Curve 100 represents the derivative of the temperature measurements of the vapor column in the neck of the distillation flask measured by the second IR sensor (i.e., the rate of change of the vapor temperature, i.e., dT$_{IRvap}$/dt).

The detection of the rising vapor temperature (T$_{IRvap}$), which occurs between stage 2 and stage 3 (See FIG. 5), is made on the basis of the observation of the variation of dT$_{IRvap}$/dt, where dT$_{IRvap}$/dt is the first derivative of T$_{IRvap}$ as a function of time, as represented by curve 76 and curve 100. Peak 80 of curve 76 in FIG. 6 (and peak 101 of curve 100 in FIG. 7) corresponds to the maximum rise in temperature value measured by the second IR sensor (i.e., the vapor temperature in the lower part of the neck of the flask).

Once T$_{IRvap}$ is detected, heat adjustments, if any, may be made, as shown in stage 3 (See FIG. 5). The adjustment applies the necessary correction of heating approximately 10-30 seconds earlier than the detection of the rising vapor by the standard vapor thermometer.

The necessary level of heating of the liquid sample is the difference between the temperature of the heating element (T$_{chauf}$) and the liquid temperature (T$_{liq}$) measured by the first IR sensor. The vapor temperature is measured by the second IR sensor T$_{IRvap}$. A monotone two-factor dependence of heating from the liquid temperature T$_{liq}$ and the difference between the liquid and vapor temperatures (all measured by IR sensors) yield the following equation:

$$(T_{chauf} - T_{liq}) = A0 + A1^{(A2 \cdot T_{liq})} + A3^{(T_{liq} - T_{IRvap})} \qquad (I)$$

where A0, A1, A2 and A3 are empirical coefficients, and in the specific case of the heating element used, these coefficients had the following values:

A0=250.2
A1=31.7
A2=6.67e-3
A3=0.47

This equation corresponds to the energy transmitted (i.e., heat) to the liquid sample and calculates the correction or adjustment of heating approximately 10-30 seconds earlier than in the prior art. The adjustment in stage 3 of the temperature of the heating element T$_{chauf}$ may be made beginning from when vapor begins to rise from the liquid sample and can be repeated every 1-2 seconds until after 2-3 mL of distillate have been collected.

Unlike the prior art, the vapor temperature is now measured by the second noncontact IR sensor and not by direct contact with the standard vapor thermometer. This second IR sensor further permits continuous measurements to be taken sooner in time and, thus, provides temperature readings to enable the operator (or automatic analyzer) to make adjustments, if necessary, to the heating temperature of the heating element to ensure the IBP and correct 5% distillation point of the liquid sample being analyzed are observed within selected standard limits.

The detection of T$_{vap}$ rising occurs between stages 3 and 4 (See FIG. 5). Detection of direct contact of hot vapors with the standard temperature sensor is made on the basis of the observation of the variation of dT$_{vap}$/dt, where dT$_{vap}$/dt is the first derivative of T$_{vap}$ as a function of time, as represented by temperature curve 78, i.e., the rate of change of the vapor temperature measured by the standard vapor thermometer. In FIG. 6, peak 82 of curve 78 corresponds to the maximum rise in temperature value measured by the standard vapor thermometer (i.e., the vapor temperature at the upper part of the neck of the distillation flask). In FIG. 7, this corresponds to peak 103 of curve 102.

As illustrated by FIGS. 6 and 7, the Time$_{vap\_step}$ may be described as the difference (in seconds) between the maximum value of dT$_{IRvap}$/dt and the maximum value of dT$_{vap}$/dt, where such difference is approximately 15 seconds. This parameter Time$_{vap\_step}$ characterizes the rate of vapor movement in the neck of the distillation flask.

Referring now to FIGS. 5, 6 and 7, once $T_{vap}$ is detected, heat adjustments, if necessary, are made. This occurs in stage 4 (See FIG. 5). This heating adjustment occurs just after $T_{vap}$ rising and before IBP detection (i.e., the first drop of distillate collected). Equation I incorporates parameter $Time_{vap\_step}$ which improves the prediction of necessary heating in the beginning of the distillation. The statistics of distillations of the products from the ASTM D86 scope with the method of the present invention (i.e., dual IR sensor measurements) provide the optimal average value for $Time_{vap\_step} \approx 15$ sec., as explained above. Variation from this value requires increasing or decreasing of the heating. As a result, the equation for stage 4 becomes:

$$(T_{chauf} - T_{liq}) = A0 + A1^{(A2 \cdot T_{liq})} + A3^{(T_{liq} - TIR_{vap})} - A4^{(Time_{vap\_step} - 15)} \quad (II)$$

where A0, A1, A2 and A3 are empirical coefficients and A4 is a new empirical coefficient. This equation demonstrates the influence of the $Time_{vap\_step}$ parameter on the calculated heating. In the specific case of the heating element used, these coefficients had the following values:
A0=243.3
A1=32.87
A2=6.796e-3
A3=0.53229
A4=4.52314

The present invention expands the scope of samples that can be analyzed with improved signal, reproducibility, and test accuracy and still remain within the prescribed limits of a selected standard. Such expanded sample types go beyond petroleum-based products and include liquid samples of non-petroleum origin (bio), IBP-high-slope products (contaminated), and high-boiling short-cuts (solvents).

The various embodiments described herein may be used singularly or in conjunction with other similar devices. The present disclosure includes preferred or illustrative embodiments in which a system and method for auto distilling liquids at strictly defined conditions regardless of composition are described. Alternative embodiments of such a system and method can be used in carrying out the invention as claimed and such alternative embodiments are limited only by the claims themselves. Other aspects and advantages of the present invention may be obtained from a study of this disclosure and the drawings, along with the appended claims.

We claim:

1. A distillation assembly for distillation of liquid samples at atmospheric pressure, said distillation assembly comprising:
   a flask having a round bottom, a neck portion and a top opening;
   a stopper for covering the top opening of said flask;
   a heating element in thermal communication with said flask for heating said flask;
   a first thermal radiation detector in optical connection with said flask;
   a second thermal radiation detector in optical connection with said flask;
   a temperature detector traversing said stopper;
   a plurality of collimators having an aperture there through, said plurality of collimators housing said first and said second thermal radiation detectors;
   a condenser connected to said flask at one end of said condenser;
   a receiving vessel/collector in communication with said condenser, said receiving vessel/collector for receiving distillate; and
   a base plate for supporting said flask, said base plate having an aperture in the center thereof and positioned between said flask and said heating element.

2. The distillation assembly, as recited in claim 1, wherein each collimator contains internal threading within said aperture.

3. The distillation assembly, as recited in claim 2, wherein said first thermal radiation detector and said second thermal radiation detector are infrared sensors.

4. The distillation assembly, as recited in claim 3, wherein said temperature detector measures temperature of a liquid sample within said flask without making contact with said sample.

5. The distillation assembly, as recited in claim 4, wherein said temperature detector measures vapor temperature of said liquid sample within said flask by direct contact with said vapor of said liquid sample.

6. The distillation assembly, as recited in claim 5, wherein said temperature detector is a thermometer.

7. The distillation assembly, as recited in claim 6, wherein said second thermal radiation detector measures temperature of the vapor of said liquid sample without making contact with said liquid sample, and said vapor being measured is located in the area between said liquid sample and said temperature detector within the neck portion of said flask.

8. The distillation assembly, as recited in claim 7, wherein said second thermal radiation detector is disposed below said temperature detector and above said first thermal radiation detector.

9. The distillation assembly, as recited in claim 8, further comprising:
   a target zone on said flask, said target zone in optical communication with said first thermal radiation detector.

10. The distillation assembly, as recited in claim 9, wherein said target zone is comprised of paint.

11. The distillation assembly, as recited in claim 10, wherein said target zone has an emissivity of at least 0.95.

12. The distillation assembly, as recited in claim 11, wherein said base plate is comprised of a metal coated glass-ceramic material.

13. The distillation assembly, as recited in claim 12, further comprising an IR matrix configured to measure a temperature of vapor in the neck portion of the flask.

14. The distillation assembly, as recited in claim 13, wherein said IR matrix is comprised of an array of IR sensors.

15. A distillation assembly, comprising:
   a flask having a bottom, a neck portion and a top;
   a heating element configured to heat the flask;
   a first thermal radiation detector configured to measure a temperature of a liquid sample located in the bottom of the flask;
   a second thermal radiation detector configured to measure a temperature of vapor at a first location in the neck portion of the flask;
   a temperature detector configured to measure the temperature of vapor at a second location in the neck portion of the flask, wherein the second location is above the first location;
   a first collimator having an aperture therethrough and configured to house the first thermal radiation detector;

a second collimator having an aperture therethrough and configured to house the second thermal radiation detector;
a condenser connected to the flask;
a receiving vessel coupled to the condenser and configured to receive distillate; and
a base plate configured to support the flask.

16. A method for automatic distillation of a liquid sample at atmospheric pressure using an automatic distillation assembly, said method comprising:
selecting a group of products to be analyzed as said liquid sample;
regulating condenser and receiver temperatures;
introducing a predefined quantity of said liquid sample to said automatic distillation assembly, said distillation assembly comprising:
  a distillation flask having a round bottom portion and a neck portion extending therefrom and a stopper for sealing said neck portion of said distillation flask;
  a target zone on said round bottom portion of said distillation flask;
  a first infrared (IR) sensor having a beam focused on said target zone;
  a second IR sensor having a beam focused on the lower portion of said neck portion of said distillation flask;
  a plurality of collimators each having an aperture therethrough, said plurality of collimators housing the first and said second IR sensors;
  a condenser removably attached at one end to said neck portion of said distillation flask;
  a thermometer traversing said stopper, said thermometer having a tip extending below said condenser;
  a cooling source surrounding said condenser;
  a collecting flask removably attached to the opposite end of said condenser;
  a base plate for supporting said distillation flask; and
  a heating element in thermal connection to said base plate;
initiating analysis with an initiating trigger;
heating said liquid sample to a predefined minimum liquid temperature within a predetermined minimum time;
heating said liquid sample to a predefined maximum liquid temperature within a predetermined maximum time;
monitoring the temperature of said liquid sample with said first IR sensor;
detecting presence of vapor from said liquid sample with said second IR sensor;
detecting vapor temperature with said second IR sensor;
adjusting heating temperature of said liquid sample based on temperature readings of said liquid sample and said vapor;
monitoring temperature of said vapor with said second IR sensor;
measuring vapor temperature of said liquid sample with said thermometer;
measuring time lapse between when said vapor is detected by said second IR sensor and when said vapor temperature is detected by said thermometer upon contact of said vapor with said thermometer; and
adjusting heating temperature of the liquid sample based on temperature readings of said liquid sample, said vapor and the difference between the temperature reading of said vapor when said vapor is detected by said second IR sensor and the temperature reading of said vapor upon contact of said vapor with said thermometer.

17. The method of claim 16, further comprising:
determining the initial boiling point of said liquid sample.

18. The method of claim 17, further comprising:
determining the 5% distillation point of said liquid sample.

19. The method of claim 18, wherein in said determining of said initial boiling point, the heating adjustment to said liquid sample is determined in accordance with the following equation:

$$(T_{chauf} - T_{liq}) = A0 + A1^{(A2 \cdot Tliq)} + A3^{(Tliq - TIRvap)},$$

wherein $T_{chauf}$ corresponds to the temperature of the heating element, Tliq corresponds to the temperature of the liquid sample measured by the first IR sensor, TIRvap corresponds to the temperature of the vapor measured by the second IR sensor and each of A0, A1, A2 and A3 corresponds to a different coefficient.

20. The method of claim 19, wherein before the initial boiling point occurs, the heating adjustment to said liquid sample is determined in accordance with the following equation:

$$(T_{chauf} - T_{liq}) = A0 + A1^{(A2 \cdot T_{liq})} + A3^{(T_{liq} - TIRvap)} - A4^{(Time_{vap\_step} - 15)},$$

wherein $Time_{vap\_step}$ corresponds to the difference in time between the maximum value of the first derivative of the vapor temperature with respect to time measured by the second IR sensor and the maximum value of the first derivative of the vapor temperature with respect to time measured by the thermometer, and A4 is a coefficient that is different from A0, A1, A2 and A3.

* * * * *